United States Patent
Hollister et al.

(10) Patent No.: US 10,624,775 B2
(45) Date of Patent: Apr. 21, 2020

(54) STRAPPING SYSTEM FOR SECURING AN ORTHOPEDIC BRACE TO THE BODY

(71) Applicant: Breg, Inc., Carlsbad, CA (US)

(72) Inventors: Matthew T. Hollister, Encinitas, CA (US); James M. Fout, Oceanside, CA (US); Serena N. Oaks, Encinitas, CA (US)

( * ) Notice: Subject to any disclaimer, the term of this patent is extended or adjusted under 35 U.S.C. 154(b) by 1070 days.

(21) Appl. No.: 14/199,976

(22) Filed: Mar. 6, 2014

(65) Prior Publication Data
US 2014/0276299 A1 Sep. 18, 2014

Related U.S. Application Data

(60) Provisional application No. 61/794,747, filed on Mar. 15, 2013.

(51) Int. Cl.
*A61F 5/01* (2006.01)

(52) U.S. Cl.
CPC .......... *A61F 5/0102* (2013.01); *A61F 5/0193* (2013.01)

(58) Field of Classification Search
CPC ........ A61F 5/0123–0127; A61F 5/0193; A61F 5/01–0113; A61F 5/0118–013; A61F 5/02–05891; A61F 5/10; A61F 5/24–3753; A61F 2005/0132–0188; A61F 2005/0197; A61F 13/00; A61F 13/06–062; A61F 13/064–108; A61F 13/12; A61F 13/128; A61F 13/14; A61F 13/143–148
USPC ................. 602/16, 23–28; 128/882
See application file for complete search history.

(56) References Cited

U.S. PATENT DOCUMENTS

| | | | |
|---|---|---|---|
| 3,046,981 A * | 7/1962 | Biggs, Jr. .............. | A61F 5/0109 602/26 |
| 4,481,941 A | 11/1984 | Rolfes | |
| 4,531,515 A | 7/1985 | Rolfes | |
| 5,002,045 A | 3/1991 | Spademan | |
| 5,368,552 A | 11/1994 | Williamson | |
| 5,421,810 A | 6/1995 | Davis | |

(Continued)

FOREIGN PATENT DOCUMENTS

| DE | 2008002943 U1 | 7/2008 |
|---|---|---|
| EP | 1588678 A1 | 10/2005 |

(Continued)

*Primary Examiner* — Keri J Nelson
*Assistant Examiner* — Michelle J Lee
(74) *Attorney, Agent, or Firm* — Rodney F. Brown

(57) ABSTRACT

A strapping system for retaining a rigid support member of an orthopedic brace in a desired utilitarian position on a body of a wearer is provided which includes a strap having a first strap end, a second strap end and an intermediate strap point between the strap ends. The strap is operatively configured to follow a strap path having a first connection point, a second connection point and a third connection point sequentially positioned on the support member. The first strap end is attached to the first connection point and the strap extends from the first connection point around the body of the wearer to the second connection point where the intermediate strap point is attached thereto. The strap is redirected at the second connection point in an opposing direction and extends back around the body of the wearer to the third connection point where the second strap end is attached thereto.

21 Claims, 7 Drawing Sheets

(56) References Cited

U.S. PATENT DOCUMENTS

| | | | |
|---|---|---|---|
| 5,562,605 A | 10/1996 | Taylor | |
| 6,039,707 A | 3/2000 | Crawford | |
| 6,361,513 B1 | 3/2002 | Rossi | |
| 6,436,066 B1 * | 8/2002 | Lockhart | A61F 5/0125 602/26 |
| 6,540,703 B1 | 4/2003 | Lerman | |
| 6,589,195 B1 | 7/2003 | Schwenn | |
| 7,087,031 B2 | 8/2006 | Rossi | |
| 7,097,627 B2 | 8/2006 | Enzerick | |
| 7,473,235 B2 | 1/2009 | Schwenn | |
| 7,749,181 B2 * | 7/2010 | Simmons | A61F 5/0109 128/882 |
| 7,775,999 B2 | 8/2010 | Brown | |
| 8,419,670 B2 | 4/2013 | Downing | |
| 2006/0178605 A1 | 8/2006 | Sauber | |
| 2010/0331750 A1 * | 12/2010 | Ingimundarson | A61F 5/0123 602/26 |
| 2011/0275970 A1 * | 11/2011 | Paulos | A61F 5/0102 602/16 |
| 2011/0295169 A1 * | 12/2011 | Hendricks | A61F 5/028 602/19 |
| 2012/0095379 A1 | 4/2012 | Hama | |
| 2013/0245523 A1 * | 9/2013 | Romo | A61F 5/0125 602/16 |

FOREIGN PATENT DOCUMENTS

| | | |
|---|---|---|
| EP | 1588678 B1 | 6/2007 |
| WO | 2009017949 A1 | 2/2009 |

* cited by examiner

STRAPPING SYSTEM FOR SECURING AN ORTHOPEDIC BRACE TO THE BODY

BACKGROUND OF THE INVENTION

The present invention relates generally to an orthopedic brace, and more particularly to a strapping system for an orthopedic brace.

Orthopedic braces embody a broad range of structures, each having the common purpose of supporting and/or stabilizing a skeletal joint when worn on the body of a user. The orthopedic brace may serve either a preventative role or a remedial role. In a preventative role, the brace provides added support and stability to a healthy skeletal joint, thereby reducing the risk of injury when the joint is subjected to undue stress. In a remedial role, the brace supports and stabilizes a skeletal joint which has been weakened by injury or other infirmity, thereby reinforcing the joint and reducing the risk of further injury while the joint is rehabilitated.

Conventional orthopedic braces typically include a frame consisting of a plurality of rigid support members positioned adjacent to the body on either side of the affected skeletal joint being stabilized. The rigid support members are dynamically interconnected by one or more rotational hinges, which are positioned adjacent to the skeletal joint being stabilized. For example, a conventional hip brace typically includes a frame having a rigid upper support member positioned adjacent to the waist and a rigid lower support member positioned adjacent to the thigh. A rotational hinge positioned adjacent to the hip joint dynamically interconnects the rigid upper and lower support members and enables the user to control the movement of the hip joint and correspondingly to control the stability of the hip joint. The hip brace typically also includes a strapping system having a plurality of straps and associated strap retainers which are either integral with brace frame or are attached thereto. The strapping system secures the brace frame to the body and maintains the brace frame in a desired position of effectiveness during use.

The present invention generally recognizes a need for an improved strapping system for an orthopedic brace which exhibits superior functional performance characteristics in securing the brace frame to the body and maintaining optimal suspension and position of the brace frame when mounted on the body of a wearer for maximum effectiveness. The present invention also recognizes a need for a strapping system which supplements the brace frame in transferring loads from the affected joint to other more stable parts of the body and in distributing the transferred load over a broad area. The present invention further recognizes a need for a strapping system which exhibits ease of tension adjustment and which facilitates the process of mounting the brace on the body or removing the brace from the body. Accordingly, it is an generally an object of the present invention to provide a strapping system for an orthopedic brace which satisfies the above-recited needs in cooperation with the brace frame. This object and others are accomplished in accordance with the invention described hereafter.

BRIEF SUMMARY OF THE INVENTION

The present invention is characterized as a strapping system for retaining a rigid support member of an orthopedic brace in a desired utilitarian position on a body of a wearer. The strapping system comprises a strap having a first strap end, a second strap end and an intermediate strap point between the first strap end and the second strap end. A preferred strap is a unitary strap. The strap is operatively configured to follow a strap path having a first connection point, a second connection point and a third connection point sequentially positioned on the support member. The first connection point is preferably a first terminus of the strap path and the third connection point is preferably a second terminus of the strap path. In accordance with other preferred alternatives, the first connection point is on a first side of the support member, the second connection point on an opposite second side of the support member and the third connection point is on the first side of the support member. In accordance with still other preferred alternatives, the first connection point is on a first cuff of the support member engaging the body of the wearer and the second connection point and third connection point are on a second cuff of the support member engaging the body of the wearer.

In any case, the first strap end of the strap is substantially attached to the first connection point. The strap path extends in a first travel direction from the first connection point around the body of the wearer to the second connection point. The intermediate strap point of the strap is substantially attached to the second connection point. The strap path is redirected at the second connection point from the first travel direction to a second travel direction opposing the first travel direction. The strap path extends in the second travel direction around the body of the wearer to the third connection point. The second strap end of the strap is substantially attached to the third connection point. The strap extending from the first connection point to the second connection point defines a first strap segment having a first strap segment length and the strap extending from the second connection point to the third connection point defines a second strap segment having a second strap segment length.

In accordance with an embodiment of the present invention, the strapping system further comprises a strap connection member slidably engaging the strap at the intermediate strap point on the strap by threading the strap twice back and forth through the strap connection member thereby doubling the strap over itself a first time at the intermediate strap point. The strap connection member effects substantial attachment of the intermediate strap point of the strap to the support member at the second connection point by releasably engaging the support member at the second connection point.

In accordance with another embodiment of the present invention, the strapping system further comprises a strap adjustment ring slidably engaging the strap at a strap adjustment ring position on the strap between the first strap end and the second strap end by threading the strap through the strap adjustment ring and reversing the direction of the strap thereby doubling the strap over itself a second time at the strap adjustment ring position.

In accordance with yet another embodiment of the present invention, the first strap segment length and/or the second strap segment length are readjustable by selecting an alternate strap adjustment ring position and slidably displacing the strap adjustment ring along the strap from the strap adjustment ring position to the alternate strap adjustment ring position. The first strap segment length and/or the second strap segment length are likewise or alternately readjustable by selecting an alternate intermediate strap point and slidably displacing the strap connection member along the strap from the intermediate strap point to the alternate intermediate strap point.

The present invention is alternately characterized as a strapping system for retaining a rigid longitudinal support assembly of an orthopedic hip brace in a desired utilitarian position on a thigh of a wearer. The strapping system comprises a thigh strap having a first strap end, a second strap end and an intermediate strap point between the first strap end and the second strap end. The thigh strap is operatively configured to follow a strap path having a first connection point, a second connection point and a third connection point sequentially positioned on the longitudinal support member. A preferred first connection point is on a first thigh cuff of the longitudinal support assembly engaging the thigh of the wearer. A preferred second connection point is on a second thigh cuff of the longitudinal support assembly engaging the thigh of the wearer. A preferred third connection point is on the second thigh cuff of the longitudinal support assembly engaging the thigh of the wearer. The first connection point is preferably on a first side of the first thigh cuff. The second connection point is preferably on a second side of the second thigh cuff, wherein the second side of the second thigh cuff opposite the first side of the first thigh cuff. The third connection point is preferably on a first side of the second thigh cuff, wherein the first side of the second thigh cuff corresponding to the first side of the first thigh cuff support member.

In any case, the first strap end of the thigh strap is substantially attached to the first connection point. The strap path extends in a substantially diagonally oriented first travel direction from the first connection point around the thigh of the wearer to the second connection point. The intermediate strap point of the thigh strap is substantially attached to the second connection point. The strap path is redirected at the second connection point from the first travel direction to a substantially horizontally oriented second travel direction opposing the first travel direction. The strap path extends in the second travel direction back around the thigh of the wearer to the third connection point. The second strap end of the thigh strap is substantially attached to the third connection point. The thigh strap extending from the first connection point to the second connection point defines a first strap segment having a first strap segment length and the thigh strap extending from the second connection point to the third connection point defines a second strap segment having a second strap segment length.

In accordance with an embodiment of the invention as presently characterized, the strapping system further comprises a strap connection member slidably engaging the thigh strap at the intermediate strap point on the thigh strap by threading the thigh strap twice back and forth through the strap connection member thereby doubling the thigh strap over itself a first time at the intermediate strap point. The strap connection member effects substantial attachment of the intermediate strap point of the strap to the longitudinal support assembly at the second connection point by releasably engaging the longitudinal support member at the second connection point.

In accordance with another embodiment of the invention as presently characterized, the strapping system further comprises a strap adjustment ring slidably engaging the thigh strap at a strap adjustment ring position on the thigh strap between the first strap end and the second strap end by threading the thigh strap through the strap adjustment ring and reversing the direction of the thigh strap thereby doubling the thigh strap over itself a second time at the strap adjustment ring position.

In accordance with yet another embodiment of the invention as presently characterized, the first strap segment length and/or the second strap segment length are readjustable by selecting an alternate strap adjustment ring position and slidably displacing the strap adjustment ring along the thigh strap from the strap adjustment ring position to the alternate strap adjustment ring position.

The present invention will be further understood from the drawings and the following detailed description.

DETAILED DESCRIPTION OF THE INVENTION

Figure 1:
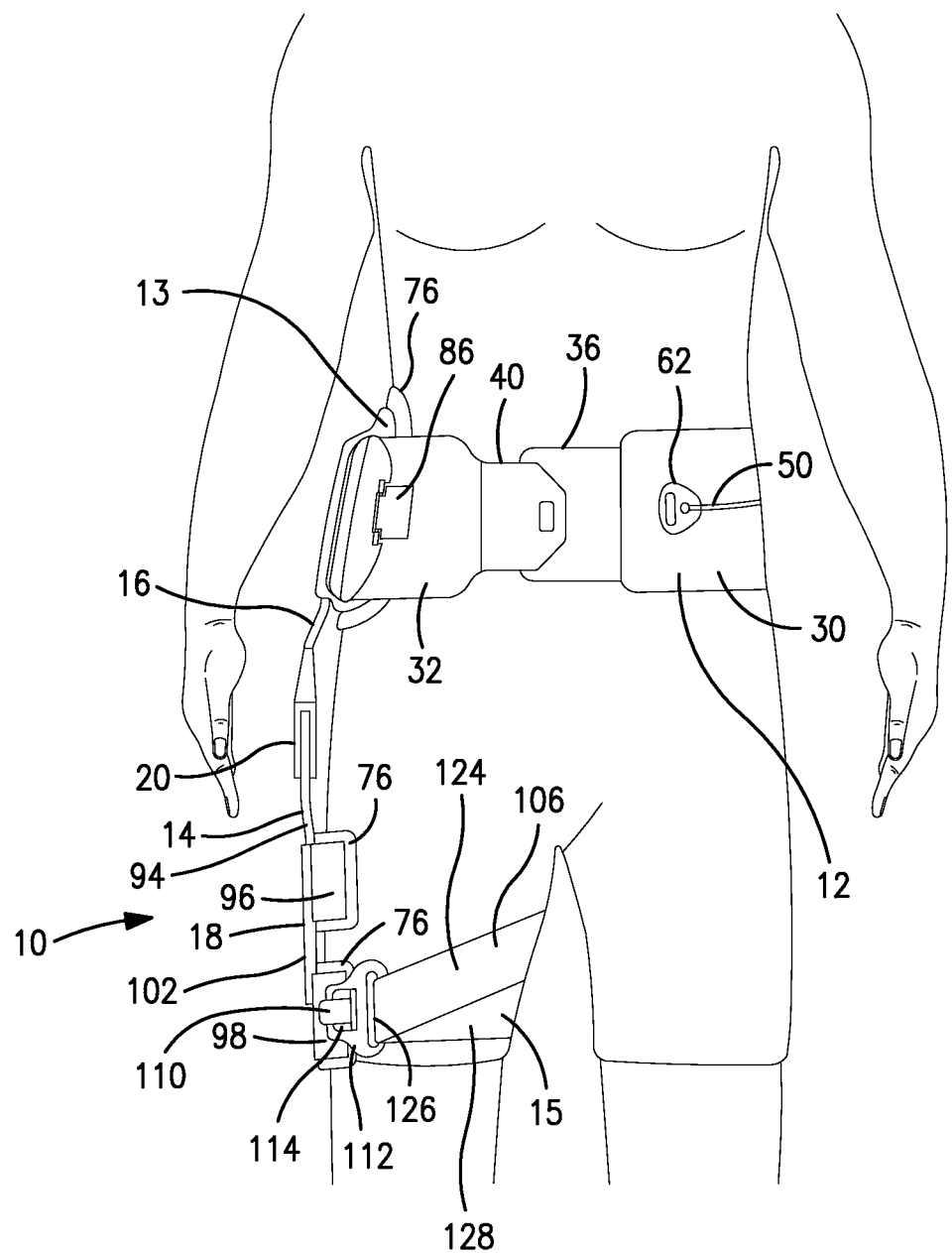
FIG. 1 is a front view of a hip brace employing a strapping system of the present invention mounted on a body of a wearer.
Figure 2:
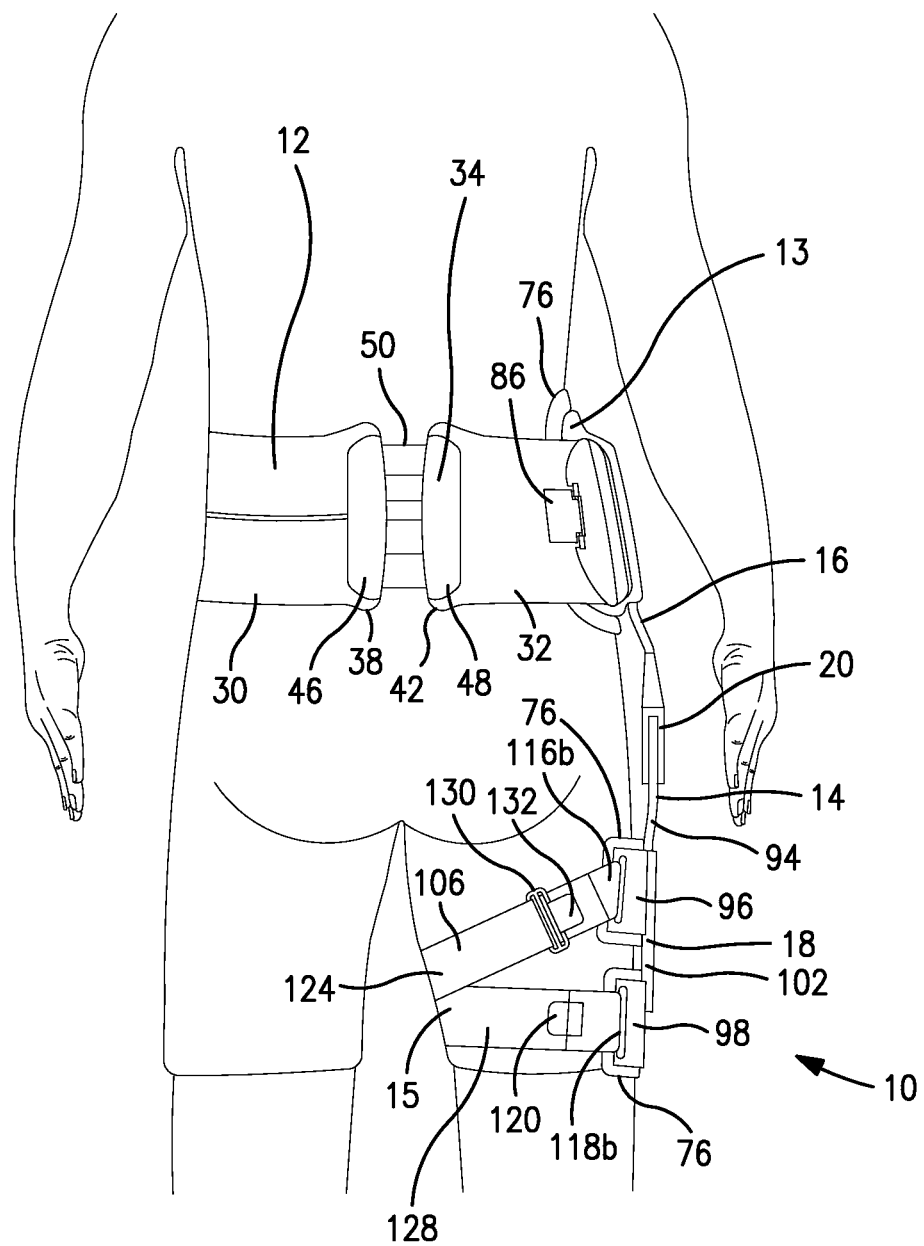
FIG. 2 is a rear view of the hip brace of FIG. 1 mounted on the body of a wearer.

The strapping system of the present invention has general utility to any orthopedic brace having a rigid support member which requires securing to the body of a wearer. The strapping system is described hereafter in use with a hip brace for purposes of illustration and by way of example. Details of a representative hip brace of the type described herein are described in pending U.S. patent application Ser. No. 13/831,676, entitled "Extension Limiting Strap for a Hip Brace" filed on Mar. 15, 2013, which is incorporated herein by reference. However, it can be appreciated by one of ordinary skill in the art applying the teaching herein that the present strapping system may alternatively be used with braces for other parts of the body and such alternative uses are within the scope of the present invention.

Referring to the above-listed FIGS., a hip brace is shown and generally designated 10. The hip brace 10 comprises a waist belt 12, a waist cuff 13, a longitudinal support assembly 14, and the strapping system 15 of the present invention. The longitudinal support assembly 14 includes a first or upper support member 16, a second or lower support member 18 and a hinge 20 rotatably joining the first and second support members 16, 18. The waist belt 12 is worn around the waist of a wearer having an affected hip joint and functions in combination with the waist cuff 13 as a first or upper anchor for the longitudinal support assembly 14. The waist belt 12 may also function in an ancillary role as a circumferential support for the lumbar region of the wearer.

As a general rule, the hip brace 10 is configured so that the waist cuff 13 and longitudinal support assembly 14 are positioned on the same side of the body of the wearer as the affected hip joint to support and stabilize the affected hip joint. In the present exemplary case shown in the drawings and described below, the affected hip joint is on the right side of the body. Accordingly, the hip brace 10 is configured so that the waist cuff 13 and longitudinal support assembly 14 are also positioned on the right side of the body. However, it is apparent to one of ordinary skill in the art that if the affected hip joint is on the left side of the body, the hinge brace 10 is readily reconfigurable so that the waist cuff 13 and longitudinal support assembly 14 can be correspondingly positioned on the left side of the body.

Figure 3:
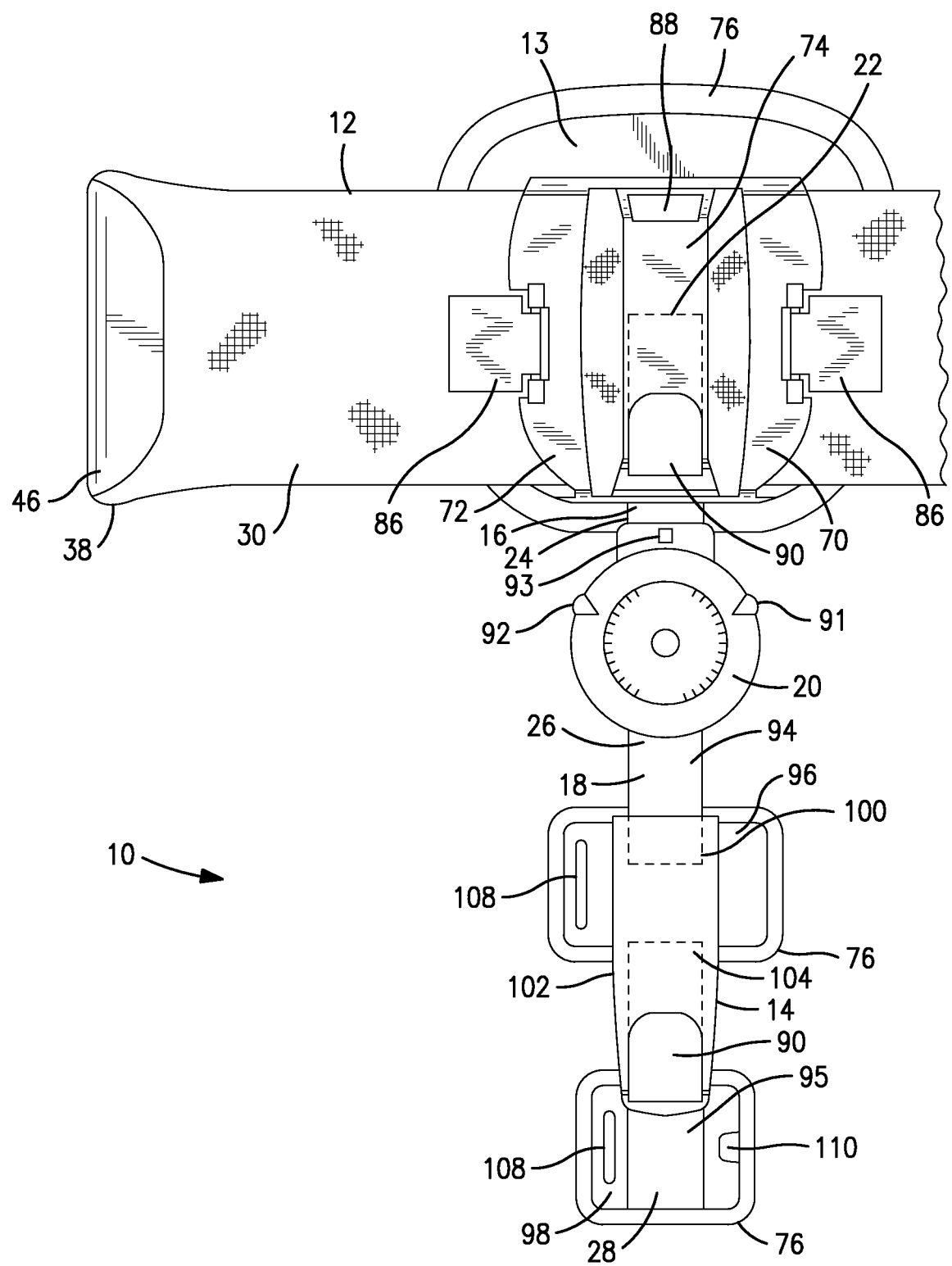
FIG. 3 is a partial plan view of the hip brace of FIG. 1 laid out flat to show the outer surface of a waist cuff and elongated longitudinal support member as well as a portion of a waist belt having utility in the present hip brace.

With particular reference to FIG. 3 and continuing reference to the remaining FIGS., the waist cuff 13 is positioned in engagement with the torso at a waist position on the right side of the waist which is immediately above the affected hip and which longitudinally aligns with the affected hip. The waist cuff 13 also engages and attaches to the waist belt 12 at this waist position. Specific details of the manner of attachment are described hereafter. The first support member 16 has a first or upper end 22 which engages and attaches to the waist cuff 13 at the waist position. The first support member 16 extends downward from its first end 22 at the waist cuff 13, extending in alignment with the longitudinal axis of the wearer's torso until the first support member 16 reaches a hip position adjacent to the affected hip joint on the right side of the body where the first support member 16 terminates.

The hinge 20 is positioned at the hip position adjacent to the hip joint and the first support member 16 has a second or lower end 24 at its lower terminus which attaches to the hinge 20. The second support member 18 has a first or upper end 26 at its upper terminus which also attaches to the hinge 20 such that the hinge 20 rotatably connects the first and second support members 16, 18 to one another enabling rotational displacement of each relative to the other. The second end 24 of the first support member 16 and the first end 26 of the second support member 18 are preferably bent or bowed slightly outward so that the hinge 20, which is typically thicker than the first or second support member 16, 18, does not unduly impinge against the hip joint. The second support member 18 extends downward from the hinge 20 along the right lateral side of the wearer's thigh until terminating at a thigh position adjacent to a point on the thigh above the knee. The lower terminus of the second support member 18 is its second or lower end 28.

Figure 4:
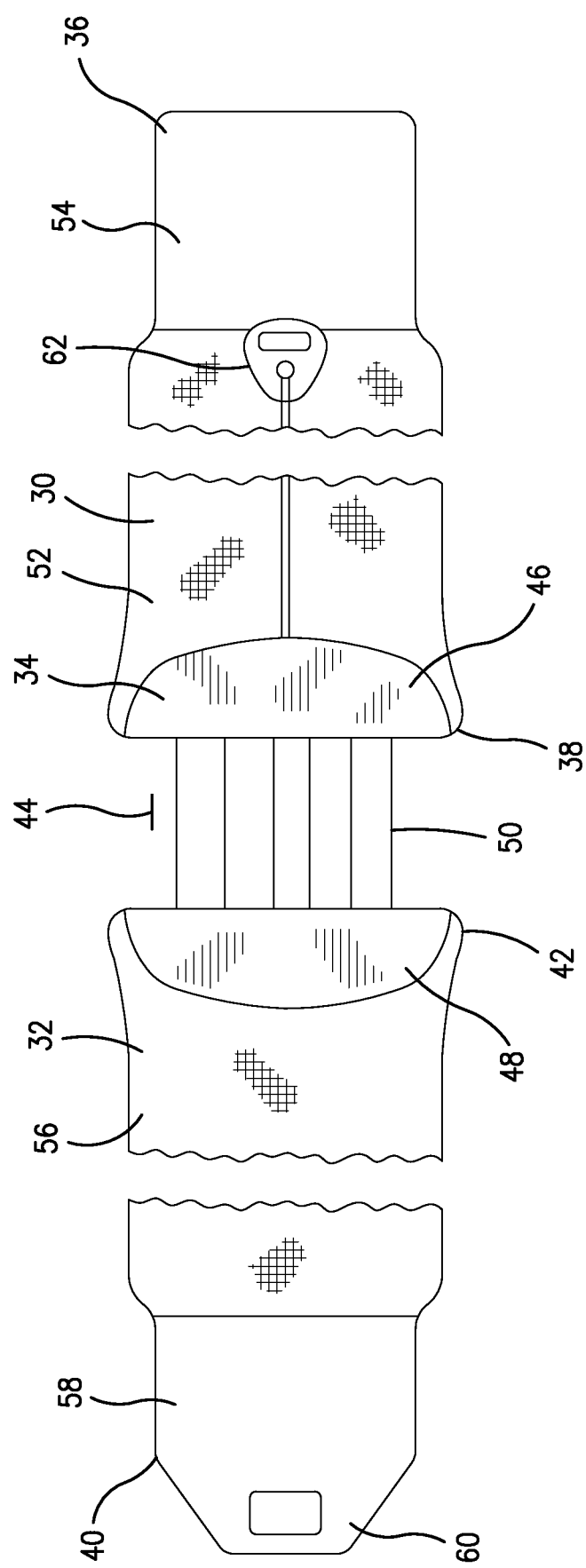
FIG. 4 is a detailed rear plan view of the waist belt of FIGS. 1-3.

The waist belt for the hip brace is not limited to any one specific configuration or construction. However, a preferred embodiment of a waist belt having utility in the hip brace is selected from a type of orthopedic supports generally known as lumbar supports or lumbar braces. A particular embodiment of a lumbar support which has utility as the waist belt 12 for the hip brace 10 is described hereafter for purposes of illustration with specific reference to FIG. 4 and continuing reference to the remaining FIGS. It is, nevertheless, understood that other lumbar supports or belt-like structures may alternatively have utility as a waist belt for the present hip brace.

The waist belt 12 is a lumbar support which resembles a conventional weightlifting belt and is configured to be worn around the waist and lumbar region of the wearer. The waist belt 12 comprises a first belt segment 30, a separate second belt segment 32 and a mechanical advantage tensioning device 34. The first belt segment 30 has two ends, namely, an attachment end 36 and an adjustment end 38, and the second belt segment 32 similarly has an attachment end 40 and an adjustment end 42. The adjustment ends 38, 42 of the first and second belt segments 30, 32, respectively, are positioned adjacent to one another on the waist belt 12, but preferably do not directly engage one another, thereby creating a discontinuity which defines a gap 44 between them.

The mechanical advantage tensioning device 34 includes a first housing 46 and a second housing 48. The first and second housings 46, 48 are positioned on either side of the gap 44, respectively, in the assembled waist belt 12. In particular, the first housing 46 is mounted on the first belt segment 30 proximal to the adjustment end 38 thereof and the second housing 48 is mounted on the second belt segment 32 proximal to the adjustment end 42 thereof. As such, the first and second belt segments 30, 32 function as an effective support base for the first and second housings 46, 48 respectively. Mounting of the housings 46, 48 on the belt segments 30, 32, respectively, may be effected by substantially permanent attachment of the housings 46, 48 to the belt segments 30, 32 using conventional permanent attachment means such as riveting, gluing, welding, sewing, stapling, screwing, or the like. Alternatively, mounting may be effected by selective releasable attachment using conventional releasable attachment means such as hook and loop fasteners (sold under the trade name VELCRO) or the like.

The mechanical advantage tensioning device 34 additionally includes a tensioning line 50. The tensioning line 50 is preferably a relatively thin (i.e., small diameter), lightweight, highly-pliant, high-strength, wear-resistant, and friction-resistant monofilament or multi-filament line. In the case of a multi-filament line, the filaments may be woven, braided or twisted together. The tensioning line 50 is also preferably relatively non-stretchable. Lines satisfying the above criteria and having utility herein are commonly characterized as cords, strings, laces, threads, wires or the like. Specific examples include lines which are constructed similar to conventional laces for recreational footwear or conventional drawstrings for window mini-blinds.

The first belt segment 30 and the second belt segment 32 are both fabricated from an at least somewhat pliant material such as cloth, laminate, solid foam, leather, or the like, which is preferably less pliant than the tensioning line 50. In any case, the material of the belt segments 30, 32 is preferably essentially non-stretchable, at least in the circular direction extending around the circumference of the waist of the wearer. In the present embodiment, the first belt segment 30 has a posterior section 52 formed from a first belt material and an anterior section 54 continuous with the posterior section 52 which is formed from a second belt material.

The first belt material is preferably a cloth/foam/cloth laminate and the second belt material is preferably a unitary pliant cloth. The cloth of both the first and second belt materials preferably has a nappy surface which can function as a loop component of a selectively releasable hook and loop fastener. This enables the user to releasably attach a corresponding hook component of a hook and loop fastener to the first belt segment 30 at essentially any point across its entire inner or outer face. In addition, the added foam layer of the first belt material renders the posterior section 52 overall thicker and less pliant (i.e., stiffer) than the anterior section 54 of the first belt segment 30. The posterior section 52 is also preferably configured with a wider footprint than the anterior section 54.

The second belt segment 32 likewise has a posterior section 56 and an anterior section 58 which are constructed in essentially the same manner as the described above with respect to the first belt segment 30. As a result of this configuration, the present embodiment of the waist belt 12 advantageously provides more support and less rearward flexibility to the lumbar region of the wearer while providing less support and more forward flexibility to the abdominal region of the wearer.

Although not shown, the first and second belt segments 30, 32, and particularly the thicker, less breathable posterior sections 52, 56 thereof, may have a plurality of small openings formed therethrough for ventilation. The thicker posterior sections 52, 56 may also have a plurality of spaced-apart grooves (also not shown) formed therein. The grooves are aligned in correspondence with the longitudinal axis of the wearer's body to provide the stiffened posterior sections 52, 56 with an articulate construction which advantageously facilitates conformance of the waist belt 12 to the arcuate contours of the wearer's body. One or more rigid reinforcing elements (also not shown) such as plates, stays or the like formed from plastics, metals, resins, composites or the like may be integrated into the waist belt 12 and more particularly into the first and/or second belt segments 30, 32 in a manner well known to one of ordinary skill in the art. The reinforcing elements can also be externally attached to the waist belt 12 as desired. In any case, any optional reinforcing elements added to the waist belt 12 preferably enhance the support function thereof.

The term "rigid", as used herein unless otherwise used as a relative term, refers to elements or materials in the hip brace 10 which have a significant degree of resistance to deformation. The term "rigid", as used herein, may also be inclusive of the term semi-rigid. As such, "rigid" elements or materials of the present invention may not undergo elastic deformation in response to a significant force or may undergo some limited degree of elastic deformation in response to a significant force in the manner of elements or materials which are conventionally termed rigid or semi-rigid in the prior art.

Each belt segment 30, 32 has a substantially similar configuration to the other. The configuration of each belt segment 30, 32 resembles a half-length of a widened belt that has been bisected along its posterior centerline. The first and second belt segments 30, 32 are preferably sized such that when their adjustment ends 38, 42 are posteriorly connected by the mechanical advantage tensioning device 34, the first and second belt segments 30, 32 and mechanical advantage tensioning device 34 in combination fully encircle the waist of the wearer. This enables the user to cinch the waist belt 12 on the body of the wearer in the following manner. The user grasps the attachment ends 36, 40 of the first and second belt segments 30, 32 respectively, and posteriorly positions the adjustment ends 38, 42 against the lower back of the wearer adjacent to the spine, but spaced apart from one another. The gap 44 between the adjustment ends 38, 42 is bridged by the mechanical advantage tensioning device 34 which connects the adjustment ends 38, 42 to one another, even while the mechanical advantage tensioning device 34 remains in a relaxed state.

The user manually wraps the length of the second belt segment 32 anteriorly around one side of the wearer's waist and pulls the attachment end 40 tight, anteriorly positioning it over the wearer's abdomen. The user likewise manually wraps the length of the first belt segment 30 anteriorly around the other side of the wearer's waist and pulls the attachment end 36 tight, anteriorly positioning it over the wearer's abdomen in overlapping relation to the attachment end 40 of the second belt segment 32. A releasable fastening tab 60 is integral with the overlapping attachment end 36 of the first belt segment 30. The fastening tab 60 has a hook component of a hook and loop fastener on its inner face. The user releasably fastens the hook component on the inner face of the fastening tab 60 to the loop component integral with the outer face of the attachment end 40 of the second belt segment 32, which is overlapped by the attachment end 36, thereby cinching the waist belt 12 on the body of the wearer. It is further understood that although a hook and loop fastener is described above as a preferred releasable fastening or attachment means for cinching the waist belt 12 on the body, other conventional releasable fasteners may have alternate utility herein such as buckles, zippers, buttons, laces and the like.

Once the waist belt 12 is anteriorly cinched on the body of the wearer, the waist belt 12 is preferably further posteriorly adjustably tensioned by means of the mechanical advantage tensioning device 34 before the wearer secures the longitudinal support assembly 14 to the body. The tensioning line 50 has two internal ends (not shown) which attach internally to the housings 46, 48. The path of the tensioning line 50 generally extends from each of its internal ends back and forth between the two housings 46, 48 as well as within the interiors of the two housings 46, 48. The midsection of the tensioning line 50 exits the interior of the second housing 48 on the lateral side thereof and loops through a tensioning handle 62. The tensioning line 50 is tensioned by pulling the tensioning handle 62 laterally, which draws the tensioning line 50 further out of the interior of the second housing 48. Conversely, the tensioning line 50 is relaxed by releasing the tensioning handle 62 and allowing the tensioning line 50 to be drawn back into the interior of the second housing 48.

Tensioning the tensioning line 50 draws the opposing first and second housings 46, 48 closer together, thereby drawing the adjustment ends 38, 42 of the underlying waist belt 12 closer together and causing the waist belt 12 to fit more snugly around the waist. Additional details of the construction and operation of the mechanical advantage tensioning device 34 are well known to one of ordinary skill in the art. An exemplary mechanical advantage tensioning device having utility with the waist belt of the present hip brace is shown and described in detail in pending U.S. patent application Ser. No. 13/831,646, entitled "Anti-Twist Mechanism for a Mechanical Advantage Tensioning Device on an Orthosis", filed on Mar. 15, 2013, which is incorporated herein by reference.

Figure 5:
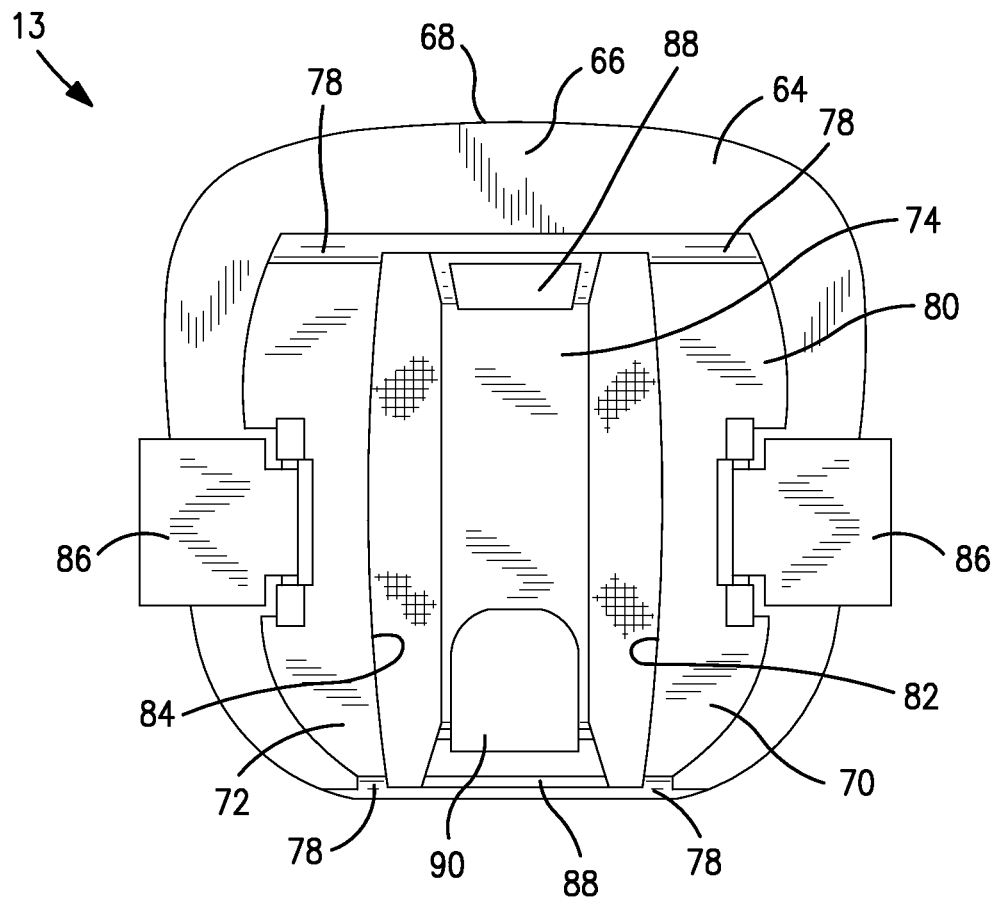
FIG. 5 is a detailed plan view of the waist cuff of FIGS. 1-3.

With specific reference to FIG. 5 and continuing reference to the remaining FIGS., the waist cuff 13 of the hip brace 10 is preferably a unitary structure having a main body 64 with an outer surface 66 and an inner surface 68. A first or anterior waist belt guide 70, second or posterior waist belt guide 72 and a first support member housing 74 are preferably integrally formed with the main body 64 on the outer surface 66 thereof. The main body 64 has a broad plate-like structure and the inner surface 68 is configured to continuously engage a broad area of the wearer's torso at the waist on the same lateral side as the affected hip joint. As such, the inner surface 68 of the main body 64 has an arcuate contour generally conforming to the curved contour on the side of the waist.

As recited above, the waist cuff 13 functions in combination with the waist belt 12 as the first anchor for the longitudinal support assembly 14. In the performance of this function, the main body 64 transfers force loads from the hinge 20 to the waist belt 12. When the wearer of the hinge brace 10 attempts to flex or extend the hip joint beyond flexion or extension limits set for the hinge 20 as described below, the longitudinal support assembly 14 applies a moment of force to the waist cuff 13 which the main body 64 transfers to the waist belt 13. This dynamic moment of force is resisted by the generally static counter-force of the waist belt 12 and the wearer's body, thereby resisting undesirable rotational or linear displacement of the waist cuff 13 relative to the wearer's torso.

During flexion, the hip joint is bent by rotating it anteriorly to decrease the angle of the joint, i.e., rotating the thigh anteriorly decreases the angle between the thigh and the torso. During extension, the hip joint is straightened by rotating it posteriorly to increase the angle of the joint, i.e., rotating the thigh posteriorly increases the angle between the thigh and the torso. The waist belt 12 and wearer's body resist the moment of force that the longitudinal support assembly 14 applies to the waist cuff 13 during flexion and extension with the objective of preventing migration of the waist cuff 13 from its desired position relative to the body. As such, the waist cuff 13 desirably remains essentially static during flexion and extension of the hip joint.

In any case, the main body 64 and the remaining elements of the waist cuff 13 recited above, whether integrally formed in a unitary construction or not, are preferably formed from one or more rigid materials, such as plastics, metals, resins, composites or the like, which are substantially less pliant than the pliant material of the waist belt 12. Due to the rigidity of the waist cuff 13, its inner surface 68 is preferably provided with a pad 76 which intervenes between the waist cuff 12 and body of the wearer to cushion the wearer from the relatively hard inner surface 68 of the waist cuff 12 when the hip brace 10 is mounted on the body. The pad 76 is formed from a relatively soft material such as a foam or the like and is preferably releasably attached to the inner surface 68 of the waist cuff 12 by means of a hook and loop fastener or the like (not shown).

The first and second waist belt guides 70, 72 are essentially identical elongate elements longitudinally aligned with the longitudinal axis of the torso. The first and second waist belt guides 70, 72 are positioned on the outer surface 66 of the main body 64 on opposite sides of the first support member housing 74. Each waist belt guide 70, 72 has a three-sided configuration with a stubbed leg 78 on each of its opposite ends which are attached to and extend a short distance away from the outer surface 66 of the main body 64. A cross member 80 extends between and connects the legs 78 of the waist belt guide 70, 72, thereby defining an open first waist belt slot 82 and an open second waist belt slot 84. The first waist belt slot 82 is between the outer surface 66 of the main body 64 and the inner surface of the first waist belt guide 70 and the second waist belt slot 84 is between the outer surface 66 of the main body and the inner surface of the second waist belt guide 72.

The first support member housing 74 is also an elongate element longitudinally aligned with the longitudinal axis of the torso. The first support member housing 74 is centrally positioned on the outer surface 66 of the main body 64 between the first and second waist belt guides 70, 72. The first support member housing 74 is likewise configured with a stubbed leg on each end to raise it above the outer surface 66 of the main body 64 in a similar manner as the first and second waist belt guides 70, 72. Raising the first support member housing 74 provides the waist belt 12 with sufficient clearance to pass underneath the first support member housing 74 between the outer surface 66 of the main body 64 and the inner surface of the first support member housing 74.

The waist cuff 13 attaches to the waist belt 12 by slidably threading the attachment end 36 of the first belt segment 30 through the first waist belt slot 82, passing the attachment end 36 under the first support member housing 74 and slidably threading the attachment end 36 through the second waist belt slot 84. The first and second waist belt guides 70, 72 each additionally include a belt lock 86 which is a flap rotatably attached to the waist belt guide 70, 72. The belt lock 86 has a hook component of a hook and loop fastener on its inner face which enables the belt lock 86 to releasably lock the waist belt 12 into place within the first and second waist belt slots 82, 84 when the belt lock 86 is rotated down onto the loop component integral with the outer surface of the waist belt 12. The belt locks 86 are similar to those shown and described in U.S. Pat. No. 8,277,403, which is incorporated herein by reference.

The first support member housing 74 is constructed with a longitudinal channel 88 formed through its interior which is shaped and sized to slidably receive the first end 22 of the first support member 16 therein. The length of the first support member 16, i.e., the distance its lower end 24 extends away from the first support member housing 74, is preferably adjustable by slidably telescoping the first support member 16 in or out of the first support member housing 74 to shorten or lengthen the first support member 16, respectively. The first support member housing 74 includes a support member lock 90 which is rotatably attached to the first support member housing 74. The support member lock 90 releasably locks the first support member 16 into place within the channel 88 at a desired length extending downward out of the channel 88 away from the waist cuff 13 and first support member housing 74 when the support member lock 90 is rotated downward to impose a pressing force against the surface of the first support member 16. The first support member 16 is unlocked for readjusting its length by rotating the support member lock 90 upward to release the pressing force against the surface of the first support member 16. The first support member housing 74 and lock 90 are similar to those shown and described in U.S. Pat. No. 8,277,403, which is incorporated above by reference.

The hinge 12 is preferably a releasably locking rotational hinge with adjustable rotation limits. As such, a preferred hinge 12 includes an adjustable flexion rotation stop 91, an adjustable extension rotation stop 92 and a releasable hinge lock 93. The adjustable flexion rotation stop 91 enables the user to limit the range of hip joint flexion by setting the flexion rotation stop 91 at a desired flexion angle limit. A typical range of hip joint angles within which the user can selectively set the flexion rotation stop 91 to a flexion angle limit is between 60° and 180°. It is noted that the hip joint is at a neutral position when the hip joint angle is 180°, e.g., when the subject is in a fully standing or fully prone position. The hip joint angle is about 90° when the subject is in a normal seated position. The adjustable extension rotation stop 92 similarly enables the user to limit the range of hip joint extension by setting the extension rotation stop 92 at a desired extension angle limit. A typical range of hip joint angles within which the user can selectively set the extension rotation stop 92 to an extension angle limit is between 110° and 190°. The releasable hinge lock 93 enables the user to releasably fix the hip joint at a single hip joint angle by selectively manually activating the hinge lock 93.

Details of an exemplary hinge having utility in the hip brace are disclosed in U.S. Pat. No. 7,235,059, which is incorporated herein by reference. Notwithstanding the above, it is understood that the present hinge is not limited to any one specific construction. Thus, many conventional hinges for orthopedic braces, which enable rotation of the first and second support members about the hinge, are alternatively employed as the hinge of the present hip brace.

The second support member 18 which extends downward from the hinge 20 along the right lateral side of the wearer's thigh is divided into two segments, i.e., a first or upper support segment 94 and a second or lower support segment 95. The second support member 18 further comprises a first or upper (proximal) thigh cuff 96 and a second or lower (distal) thigh cuff 98.

Figure 6:
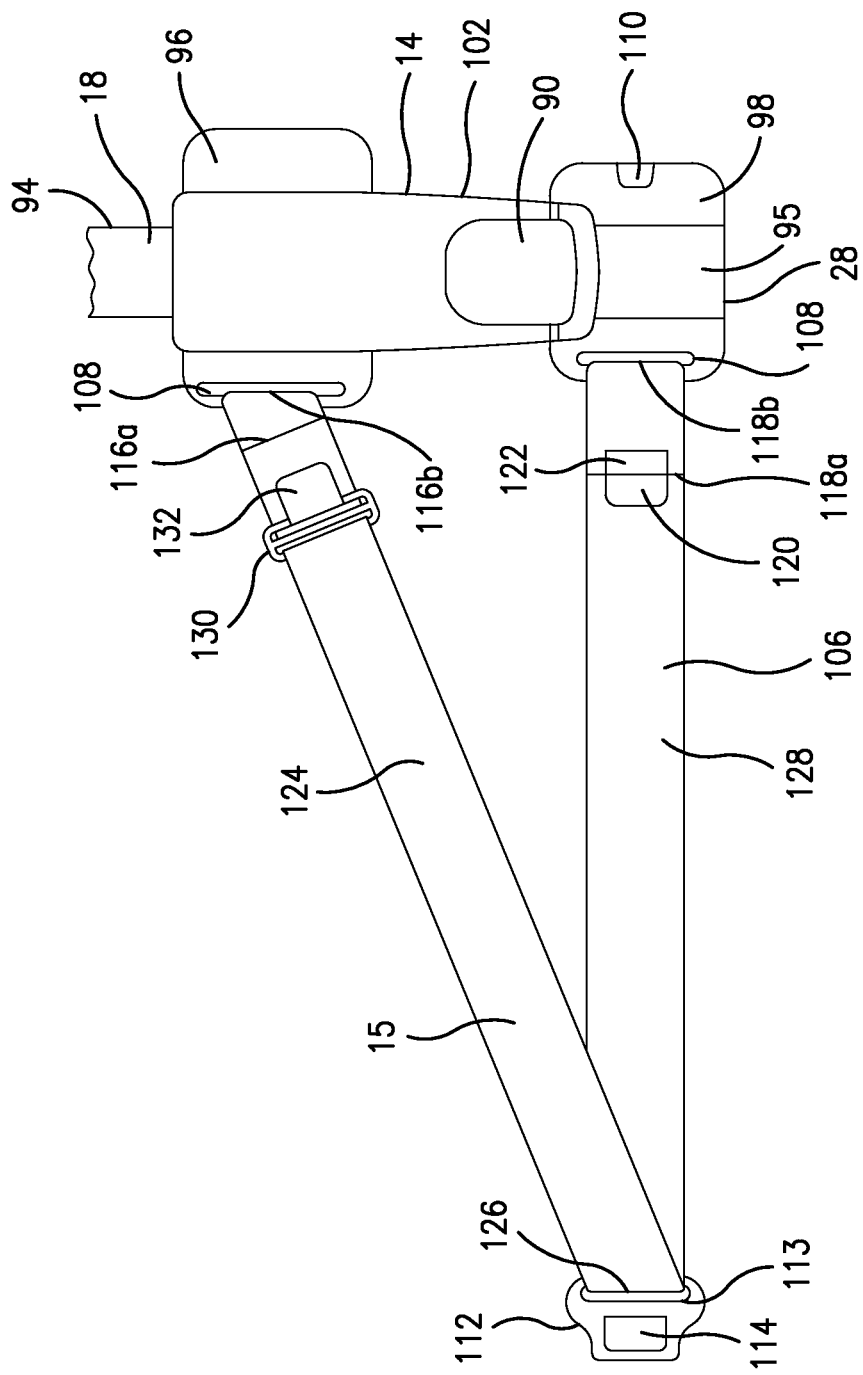
FIG. 6 is a detailed plan view of the operatively configured strapping system of the present invention and associated thigh cuffs and lower support member laid out flat to show their outer surface.
Figure 7:
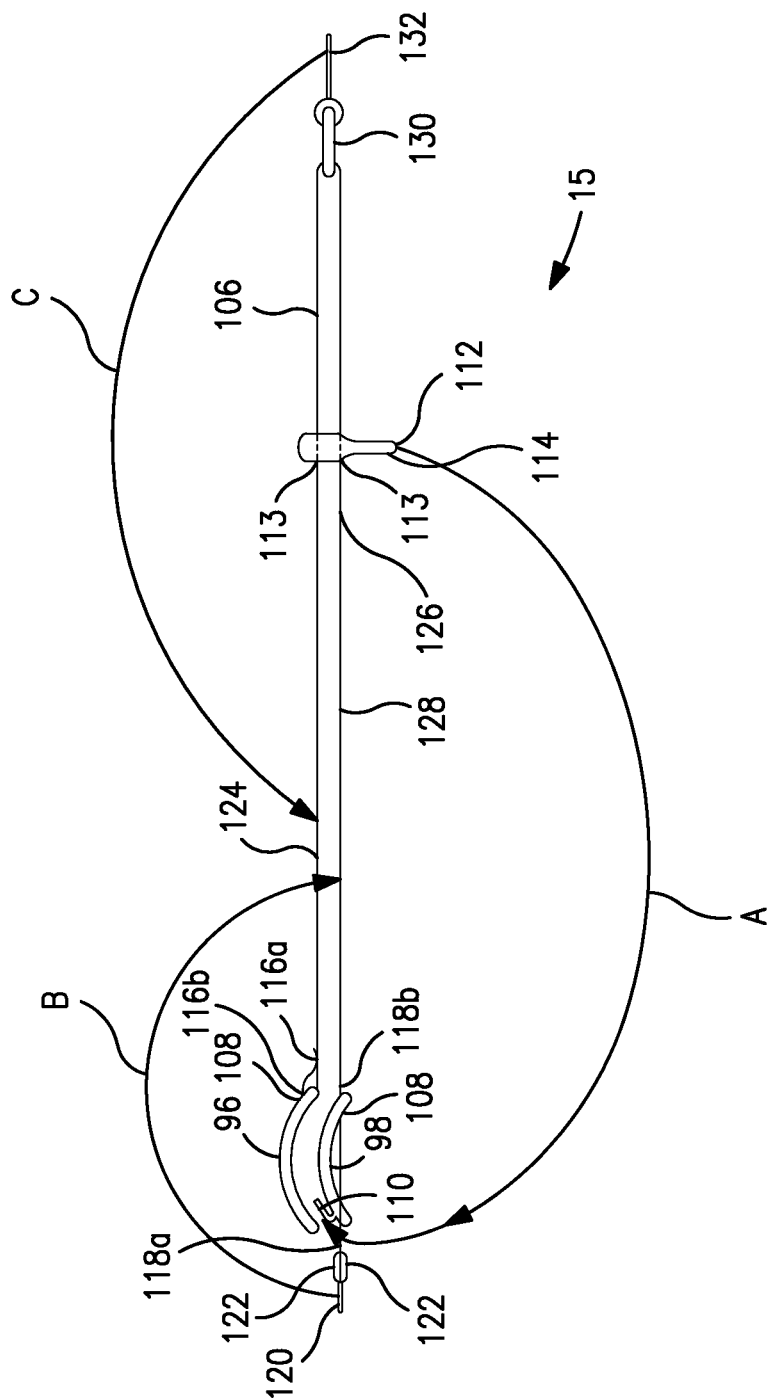
FIG. 7 is a top view of the operatively configured strapping system of the present invention and associated thigh cuffs.

The second support member 18 is preferably secured to the wearer's thigh by the thigh strapping system 15 of the present invention which is described hereafter with specific reference to FIGS. 6 and 7 and continuing reference to the remaining FIGS. The thigh strapping system 15, in cooperation with the first and second thigh cuffs 96, 98, functions as a second or lower anchor for the longitudinal support assembly 14. Each first and second thigh cuff 96, 98 has an arcuate configuration with a concave inner surface to conform to the contour of the wearer's thigh. The inner surface of each first and second thigh cuff 96, 98 is preferably provided with a pad 76 of the type described above which intervenes between the first and second thigh cuffs 96, 98 and body of the wearer to cushion the wearer from the relatively hard inner surfaces of the first and second thigh cuffs 96, 98. As such, the inner surface of each first and second thigh cuff 96, 98 and associated pad 76 fits closely and continuously against the thigh, thereby providing a broad cushioned contact surface for the hip brace 10 to engage the thigh and, more particularly, to connect the longitudinal support assembly 14 with the thigh in a manner described below.

The first support segment 94 of the second support member 18 has a first or upper end which attaches to the hinge 20. The first end of the first support segment 94 is the same structural element as the first end 26 of the second support member 18 and, as such, is identified hereafter and in the FIGS. by the same reference number. The first support segment 94 also has a second or lower end 100 which is fixably attached to the first thigh cuff 96. The first thigh cuff 96 includes a second support member housing 102 which has a substantially similar construction to the first support member housing 74. As such, the second support member housing 102 also has essentially the same longitudinal channel 88 formed through its interior. The second support segment 95 of the second support member 18 has a first or upper end 104 and the channel 88 of the second support member housing 102 is shaped and sized to slidably receive the first end 104 therein. Accordingly, the first thigh cuff 96 connects the first and second support segments 94, 95. The length of the second support segment 95 extending downward out of the channel 88 away from the second support member housing 102 is preferably telescopingly adjustable in substantially the same manner as described above with respect to the telescopingly adjustable length of the first support member 16. As such, the second support member housing 102 has essentially the same support member lock 90 as the first support member housing 74. The second support segment 95 of the second support member 18 has a second or lower end which is preferably fixably attached to the second thigh cuff 98. The second end of the second support segment 95 is the same structural element as the second end 28 of the second support member 18 and, as such, is identified hereafter and in the FIGS. by the same reference number.

In addition to providing a contact surface for the rigid brace components to engage the body, the first and second thigh cuffs 96, 98 also function as strap retainers, cooperating with a thigh strap 106 of the present strapping system 15 to secure the hip brace 10 and, more particularly, the longitudinal support assembly 14, to the body of the wearer. The thigh strap 106 is preferably a unitary strap, wherein the term "unitary strap" is used herein to characterize a continuous unbroken length of a single long strap which is free from overlaps when laid out flat in a non-operative configuration, but which at least partially doubles over, i.e., overlaps, itself one or more times when it is operatively configured to shorten its effective length.

In their capacity as strap retainers, the first and second thigh cuffs 96, 98 provide means for directing the path of the thigh strap 106 and for connecting the thigh strap 106 to the hip brace 10 and, more particularly, to the longitudinal support assembly 14. Although the first thigh cuff 96 of the present embodiment enables both of the above-recited functions within a single integrated construction, it is also within the scope of the present invention to substitute this integrated construction with multiple separate, but cooperative, structures which perform the same functions as the single integrated structure of the first thigh cuff 96. The same applies to the second thigh cuff 98 as well.

In any case, a first or posterior side of each first and second thigh cuff 96, 98 has a cuff strap retention opening 108 integrally formed therein, through which the thigh strap 106 is threaded in a manner described below to define, at least in part, the path of the thigh strap 106. A second or anterior side of the second thigh cuff 98 is also provided with a hook-shaped strap connection catch 110. The strapping system 15 is further provided with a releasable strap connection member 112 which functions in cooperation with the strap connection catch 110 in a manner described below. The releasable strap connection member 112 is preferably constructed from a rigid material, examples of which are recited above. The releasable strap connection member 112 has a bifurcated strap retention opening 113 and a strap connection opening 114 integrally formed therein. The thigh strap 106 is threaded through both sides of the bifurcated strap retention opening 113 by first threading the thigh strap 106 through one side of the strap retention opening 113, doubling the thigh strap 106 back over itself at a point past the strap connection member 112, and threading the thigh strap 106 back through the other side of the strap retention opening 113 in the opposite direction to retain the strap connection member 112 in slidable engagement with the thigh strap 106. The strap connection catch 110 and strap connection opening 114 in combination provide the strapping system 15 with a means for releasably coupling the thigh strap 106 with the second thigh cuff 98 and correspondingly with the second support member 18 in a manner described below. Cuff strap retention openings 108 and releasable strap couplings 110, 114 of the type described above are disclosed in detail in U.S. Pat. No. 8,277,403.

When the thigh strap 106 of the present strapping system 15 is laid out flat with no overlaps in a non-operative configuration, it has a free first strap end 116*a* and an opposite free second strap end 118*a*. The thigh strap 106 is preferably fabricated from a pliant material such as cloth, laminate, leather, or the like, which may be the same or similar to the pliant material used in the waist belt 12. The thigh strap 106 is also preferably essentially non-stretchable, at least in the longitudinal direction of the thigh strap 106. The surface of the thigh strap 106 is preferably integrally formed from a nappy material functioning as the loop component of a hook and loop fastener. Alternatively, the thigh strap 106 is preferably supplemented with a swath of the loop component which continuously extends across essentially the length of the surface of the thigh strap 106.

A patch of the hook component is also preferably connected to at least one free strap end 116a, 118a of the thigh strap 106.

Connection of the patch of hook component to the free strap end 116a, 118a of the thigh strap 106 may be effected by integration of the patch of hook component with the free strap end 116a, 118a of the thigh strap 106, by fixed attachment (i.e., substantially permanent) of the patch of hook component to the free strap end 116a, 118a of the thigh strap 106 or by releasable attachment (e.g., by means of hook and loop fastening) of the patch of hook component to the free strap end 116a, 118a of the thigh strap 106. This enables the user to double the thigh strap 106 over itself at least part way and releasably fasten a free strap end 116a, 118a of the thigh strap 106 having the patch of the hook component connected thereto to the underlying surface of the thigh strap 106 at a desired position on the surface by means of the hook and loop fastener, thereby enabling the user to adjustably shorten the overall length of the thigh strap 106 as desired.

It is readily apparent that the locations of the hook components and the loop components associated with the free strap end 116a, 118a of the thigh strap 106 and the surface of the thigh strap 106, respectively, can be reversed within the scope of the present invention so long as a hook component of either the surface of the thigh strap 106 or free strap end 116a, 118a of the thigh strap 106 aligns with a loop component of the other at a desired position. In the present embodiment, the patch of hook component is in the form of a releasable first hook component tab 120 is which connected to the free second strap end 118a of the thigh strap 106 by a connected pair of butterflying hook component releasable attachment tabs 122. However, it is understood that a patch of hook component can be alternatively connected to the free first strap end 116a of the thigh strap 106 in any conventional manner within the teaching of the present invention.

When the hip brace 10 is mounted on the body of a wearer and the strapping system 15 is correspondingly operatively configured, the thigh strap 106 follows a strap path having a first terminus and a second terminus. The strap path begins at the first terminus with connection of the thigh strap 106 to the first thigh cuff 96 at a first strap connection point which coincides with the cuff strap retention opening 108 in the first or posterior side of the first thigh cuff 96. Thus, the cuff strap retention opening 108 in the first or posterior side of the first thigh cuff 96 is alternately termed a first strap connector. Connection is effected in the present embodiment by threading the free first strap end 116a of the thigh strap 106 through the cuff strap retention opening 108 integral with the first thigh cuff 96, doubling the free first strap end 116a back over the thigh strap 106 a short distance and effectively permanently attaching the thigh strap 106 to the first thigh cuff 96 at the first strap connection point by sewing or otherwise permanently attaching the free first strap end 116a to the thigh strap 106 after it has been doubled over. Although not shown, it is alternatively within the scope of the present invention to releasably rather than permanently attach the free first strap end 116a to the thigh strap 106 after it has been doubled over by means of a patch of hook component provided at the free first strap end 116a of the thigh strap 106 which the user releasably attaches to the loop component on the surface of the thigh strap 106 after doubling the free first strap end 116a over the thigh strap 106.

In yet another alternative not shown, a short closed ringlet of pliant strap material is threaded through the cuff strap retention opening 108 as well as through a separate conventional rigid strap ring so that the closed ringlet is permanently and slidably retained on both the first thigh cuff 96 and strap ring. The thigh strap 106 is then connected to the first thigh cuff 96 at the first strap connection point by threading the free first strap end 116a through the strap ring and looping it around back onto itself, thereby permanently or releasably attaching it to the strap ring in the manner described above and correspondingly, connecting the free first strap end 116a to the first thigh cuff 96 via the closed ringlet of strap material.

In all of the above cases, it is understood that when the thigh strap 106 is operatively configured with the free first strap end 116a doubled over the thigh strap 106, there is a point on the thigh strap 106 coinciding with the position of the first connection point of the strap path which is also the first terminus of the strap path. This point on the thigh strap 106 where it substantially reverses direction doubling back is identified by reference number 116b and is termed the fitted first strap end. Stated in the alternative, the first fitted strap end 116b is the point on the thigh strap 106 where the thigh strap 106 engages the cuff strap retention opening 108 in the first or posterior side of the first thigh cuff 96. Furthermore, it is understood that alternately characterizing the thigh strap 106 and/or, more particularly, the fitted first strap end as being "substantially attached" to the first thigh cuff 96 encompasses each of the above-recited embodiments including the embodiment where the first strap end is not directly attached or directly connected to the first thigh cuff 96, but is indirectly connected to the first thigh cuff 96 via only a single very short de minimis intervening link as described above.

The strap path is further characterized as having a first strap segment 124, an fitted intermediate strap point 126 and a second strap segment 128. The first and second strap segments 124, 128 extend back and forth between the first and second thigh cuffs 96, 98 and intervening fitted intermediate strap point 126 to form an acute angle termed the travel angle. The first strap segment 124 is substantially diagonally oriented, having an angled path relative to the ground and, as such, is alternately termed a diagonal leg of the strap path. The first strap segment extends in a first travel direction from the fitted first strap end on the first or posterior side of the first thigh cuff 96, i.e., the first terminus of the strap path, along a downward spiral path sequentially across the posterior, medial and anterior sides of the thigh to a second strap connection point on the second or anterior side of the second thigh cuff 98. The travel angle of the thigh strap 106 in the first strap segment is adjustable by adjusting the length of the second support member 18 and/or the length of the thigh strap 106 in a manner described herein. As such, the travel angle is adjusted to avoid the crotch area of the wearer. In particular, the travel angle is adjusted so that the thigh strap 106 is positioned in a non-irritating area just above the vastus medialis and below the quadriceps muscles.

The fitted intermediate strap point 126 on the thigh strap 106 between the first and strap connection points and correspondingly between the first and second termini of the strap path is releasably connected to the second thigh cuff 98 at the second strap connection point on the second or anterior side of the second thigh cuff 98 by means of the strap connection member 112 which is slidably positioned on the thigh strap 106 at the fitted intermediate strap point 126. Thus, the strap connection member 112 and the cooperative structure on the second or anterior side of the second thigh cuff 98 which connects with the member 112 and is described below are alternately termed a second strap connector. The path that the strap connection member 112 follows to the second thigh cuff 98 which enables their releasable connection is depicted by arrow A in FIG. 7. The area bounded on the bottom by arrow A and bounded on the top by the first and second strap segments 124, 128 of the thigh strap 106 is occupied by the thigh of a wearer when the hip brace 10 is mounted on the body of the wearer and the strapping system 15 is operatively configured. In the present embodiment, the position of the fitted intermediate strap point 126 on the thigh strap 106 is where the thigh strap 106 is doubled over itself twice at essentially the same locale. In particular, the thigh strap 106 is doubled over a first time when it passes back and forth through the strap retention opening 113 of the strap connection member 112 as described above and is doubled over a second time at essentially the same locale in a manner which employs a strap adjustment ring described below. As a result, there are four overlapping layers of the thigh strap 106 termed the fitted paired intermediate strap connection points which are in the immediate proximity of the fitted intermediate strap point 126 where the first and second strap segments 124, 128 overlap one another.

Connection of the thigh strap 106 to the second thigh cuff 98 at the second strap connection point is effected by lowering the strap connection opening 114 over the strap connection catch 110 at the second strap connection point so that the strap connection catch 110 extends through the strap connection member 112 and the edge of the strap connection opening 114 engages the strap connection catch 110. It is understood that alternately characterizing the thigh strap 106 and/or, more particularly, the intermediate strap point 126 of the thigh strap 106 as being "substantially attached" to the second thigh cuff 98 encompasses the present embodiment where the intermediate strap point 126 of the thigh strap 106 is not directly attached or directly connected to the second thigh cuff 98, but is indirectly releasably connected to the second thigh cuff 98 via only the relatively short strap connection member 112.

The strap path continues along the second strap segment 128 which is substantially horizontally oriented, having a non-angled path aligned parallel to the ground. As such, the second strap segment 128 is alternately termed a horizontal leg of the strap path. The second strap segment substantially reverses direction from the first travel direction of the first strap segment and follows a second travel direction opposing the first travel direction which has a substantially non-angular straight circumferential horizontal path. As such, the second strap segment extends from the intermediate strap point 126 sequentially back around the anterior, medial and posterior sides of the wearer's thigh to a third strap connection point where the strap path terminates at the second terminus. The third strap connection point coincides with the cuff strap retention opening 108 in the first or posterior side of the second thigh cuff 98. Connection is effected in the present embodiment by threading the free second strap end 118a through the cuff strap retention opening 108 integral with the second thigh cuff 98, doubling the free second strap end 118a back over the thigh strap 106 and releasably attaching the thigh strap 106 to the second thigh cuff 98 at the third strap connection point by engaging the hook component tab 120 on the free second strap end 118a to the thigh strap 106 after it has been doubled over the thigh strap 106. The path that the hook component tab 120 follows to the thigh strap 106 which enables their releasable attachment is depicted by arrow B in FIG. 7.

Although not shown, it is alternatively within the scope of the present invention to permanently, rather than releasably, connect the doubled over the free second strap end 118a in the same manner as described above with respect to free first strap end 116a of the thigh strap 106 and the first thigh cuff 96. In yet another alternative not shown, a short closed ringlet of pliant strap material and additional strap ring are employed to connect the free second strap end 118a of the thigh strap 106 to the second thigh cuff 98 in the same manner as described above with respect to free first strap end 116a of the thigh strap 106 and the first thigh cuff 96.

In all of the above cases, it is understood that when the thigh strap 106 is operatively configured with the free second strap end 118a doubled over the thigh strap 106, the second strap end of the thigh strap 106 is redefined as point on the thigh strap 106 coinciding with the position of the third connection point which is also the second terminus of the strap path. Accordingly, when the thigh strap 106 is in the operative configuration, the second strap end is the point on the thigh strap 106 where it substantially reverses direction doubling back on itself and the second strap end is identified by reference number 118b. Stated in the alternative, the second strap end 118b is the point on the thigh strap 106 where the thigh strap 106 engages the cuff strap retention opening 108 in the first or posterior side of the second thigh cuff 98. Furthermore, it is understood that alternately characterizing the thigh strap 106 and/or, more particularly, the second strap end as being "substantially attached" to the second thigh cuff 98 encompasses each of the above-recited embodiments including the embodiment where the second strap end is not directly attached or directly connected to the second thigh cuff 98, but is indirectly connected to the second thigh cuff 98 via only a single very short de minimis intervening link as described above.

It is apparent that the user is able to adjust the overall length of the thigh strap 106 at the third strap connection point when the second strap end is releasably connected to the second thigh cuff 98 in accordance with the embodiment shown in the FIGS. Adjustment of the length of the thigh strap 106 is effected by adjusting the distance that the free second strap end 118a of the thigh strap 106 is doubled over after it has been threaded through the cuff strap retention opening 108, but before it is releasably attached to the thigh strap 106. Releasable attachment of the free second strap end 118a to the thigh strap 106 in the above manner results in two overlapping layers of the thigh strap 106 along a substantial portion of the second strap segment 128 (i.e., horizontal leg) extending away from the third strap connection point. The user is also able to adjust the overall length of the thigh strap 106 in a similar manner at the first strap connection point if its first strap end is releasably connected to the first thigh cuff 96 (not shown) rather than permanently connected as shown in the embodiment of the FIGS.

The strapping system 15 provides another means of adjusting the overall length of the thigh strap 106 which employs the strap connection member 112 and a strap adjustment ring 130. The strap adjustment ring 130 is preferably constructed from a rigid material such as the material of the releasable strap connection member 112. As noted above, the strap connection member 112 is slidably retained on the thigh strap 106 by threading the thigh strap 106 through one side of the bifurcated strap retention opening 113, around the post dividing the strap retention opening 113 and back out the other side of the strap retention opening 113. As such, the strap connection member 112 is slidably displacable along the length of the thigh strap 106 while being retained thereon. The strap adjustment ring 130 is likewise slidably retained on the thigh strap 106 such that the strap connection member 112 is positioned between the strap adjustment ring 130 and the first strap connection point of the thigh strap 106 on the first thigh cuff 96 when the hip brace 10 is mounted on the body with the strapping system 15 configured about the thigh. The strap adjustment ring 130 is also slidably displacable along the length of the thigh strap 106, but slidable independent of the strap connection member 112.

The user shortens the length of the thigh strap 106 in accordance with the present adjustment means by drawing the thigh strap 106 through one side of the strap retention opening 113 away from the first or second thigh cuff 96, 98 without correspondingly feeding the thigh strap 106 out the other side of the strap retention opening 113 toward the first or second thigh cuff 96, 98. A strap overlap loop is formed in the thigh strap 106 on the opposite side of the strap connection member 112 from the first and second thigh cuffs 96, 98, which is secured by sliding the strap adjustment ring 130 to the midpoint of the strap overlap loop of the thigh strap 106 and releasably attaching another hook component tab 132, which is attached or otherwise connected to the strap adjustment ring 130 at a fitted ring point, to an underlying segment of the thigh strap 106. As such, the location of this coupling is termed a fitted ring point coupling point. The path that the hook component tab 132 follows to the thigh strap 106 which enables their releasable attachment is depicted by arrow C in FIG. 7. This procedure is essentially reversed to increase the length of the thigh strap 106. As a result, there are three overlapping layers of the thigh strap 106 along a substantial portion of the first strap segment 124 (i.e., diagonal leg) where the first and second strap segments 124, 128 are no longer in overlapping relation with one another.

In summary, the strapping system of the present invention can be used in one embodiment as a thigh strapping system for a hip brace. An applicable hip brace comprises a waist belt, a waist cuff, a rigid frame and the present thigh strapping system. The frame includes two rigid elongate members, two thigh cuffs engaging one of the elongate members and a hinge. The frame spans a side of a wearer and connects to the thigh of the wearer via the strapping system and connects to the waist of the wearer via the waist belt. The hinge is positioned between the two rigid members and rotatably connects them, thereby controlling the range of motion of the wearer's hip joint. The thigh strapping system includes a strap extending between the two thigh cuffs along a strap path which extends back and forth along a diagonal leg and a horizontal leg around the posterior of the wearer's thigh. The thigh cuffs function as strap retainers to retain the strapping system in connection with the rigid frame and correspondingly the waist cuff and belt. The waist cuff and thigh cuffs desirably transfer loads from the hinge to the waist belt and the thigh strap. If the hip joint flexes or extends to flexion or extension angles, respectively, which are at the flexion or extension limits the user has set at the hinge, the waist cuff and thigh cuffs receive moments of force that are restricted by the tension of the belt and thigh straps wrapped around the wearer's body. The thigh strapping system of the present invention effectively transfers the loads of these moments of force away from the hip joint and onto the wearer's thigh.

The present strapping system provides control of both the proximal and distal cuffs which ensures that the hinge remains in a position over the center of rotation of the wearer's hip joint and ensures that the load from the hinge is dispersed over a greater area of the wearer's leg. This greatly improves the comfort of the brace. The strapping system can be precisely fit to the patient due to the adjustable length of the rigid elongate member to which the distal thigh cuff is attached, thereby avoiding uncomfortable strap contact with the medial crotch area. The present strapping system also requires releasable attachment or detachment of the strap to the frame at only one point to put on or take off the brace, which improves the wearer's ease of use. The releasable strap connection point is described above as the second strap connection point on the second or anterior side of the distal cuff. This operative configuration of the strapping system enables the user to adjust the lengths of both the angled strap segment (i.e., diagonal leg) and circumferential strap segment (i.e., horizontal leg) of the one-piece thigh strap with a single pull on the strapping system by the user.

The present strapping system provides several advantages over prior art strapping systems. In particular, the present strapping system provides improved control over the position of the hinge by tensioning when the user attempts to flex his/her leg past the allowable flexion angle limit of the hinge, thereby holding the hinge in place. Without the present strapping system, the hinge is able to translate forward and the wearer is able to undesirably flex the hip joint past the allowable flexion angle limit. The present strapping system also controls the hinge while avoiding irritating the sensitive crotch area of the wearer. The strapping system allows the thigh strap to be positioned between the vastus medialis and quadriceps muscles which helps to secure the distal cuff in place on the user's leg. The combination of the telescoping thigh cuff and adjustable angled strap segment (i.e., diagonal leg) spanning from the proximal to the distal cuff makes this positioning possible. The present strapping system also provides control of both the proximal and distal cuffs and, as a result, better control of the wearer's hip flexion/extension with only one point of attachment and adjustment for the user.

While the forgoing preferred embodiments of the invention have been described and shown, it is understood that alternatives and modifications, such as those suggested and others, may be made thereto and fall within the scope of the invention.

We claim:

1. A strapping system for an orthopedic brace comprising:
   a strap having a fitted first strap end, a fitted second strap end and a fitted intermediate strap connection point between said fitted first and second strap ends;
   a strap connection member slidably engaging said strap;
   a rigid support member having a first strap connector, a second strap connector and a third strap connector, wherein said first and third strap connectors are linearly aligned with one another to define a first-third strap connector line segment extending from said first strap connector to said third strap connector;
   wherein said strapping system is adapted to selectively transition between an operative configuration adapted to be worn on a body of a wearer and a non-operative configuration adapted to be off any body of any wearer;
   when said strapping system is in said operative configuration: said strap is adapted to wrap around the body and retain said rigid support member in engagement with the body, said fitted first strap end is substantially attached to said first strap connector, said strap connection member slidably engages said fitted intermediate strap connection point and is releasably attached to said second strap connector, thereby effecting releasable substantial attachment of said fitted intermediate strap connection point to said second strap connector, said fitted second strap end is substantially attached to said third strap connector, said fitted first strap end and said fitted intermediate strap connection point bound a first strap segment having a first strap segment length, said fitted intermediate strap connection point and said fitted second strap end bound a second strap segment contiguous with said first strap segment and having a second strap segment length, said first strap segment, said second strap segment and said first-third strap connector line segment in combination define a triangular shape and said first strap segment length and said second strap segment length have a sum defining a strap length;

when said strapping system is in said non-operative configuration: said strap connection member is detached from said second strap connector, thereby effecting detachment of said strap from said second strap connector, said strap is adapted to unwrap from around the body and said rigid support member is adapted to disengage from the body, said fitted first strap end is substantially attached to said first strap connector, said strap connection member slidably engages said strap and said fitted second strap end is substantially attached to said third strap connector;

wherein said strapping system is adapted to transition from said operative configuration to said non-operative configuration by detaching said strap connection member from said second strap connector, thereby detaching said strap from said second strap connector, adapting said strap to unwrap from around the body and adapting said rigid support member to disengage from the body;

wherein said strapping system is adapted to transition from said non-operative configuration back to said operative configuration by adapting said rigid support member to re-engage with the body, adapting said strap to re-wrap around the body and releasably re-attaching said strap connection member to said second strap connector, thereby effecting releasable substantial re-attachment of said fitted intermediate strap connection point to said second strap connector; and wherein said fitted first strap end remains substantially attached to said first strap connector, said strap connection member slidably engages said strap and said fitted second strap end remains substantially attached to said third strap connector during transition from said operative configuration to said non-operative configuration.

2. The strapping system of claim 1, wherein said rigid support member is a first rigid support member and said strapping system further includes a second rigid support member rotatably connected to said first rigid support member by a rotatable hinge.

3. The strapping system of claim 2, wherein said first rigid support member is adapted to be positioned on a first side of a rotatable joint of the body in engagement with a limb of the body rotationally displaceable about the rotatable joint and is adapted to move in correspondence with the limb, said second rigid support member is adapted to be positioned on a second side of the rotatable joint opposite the first side in engagement with the body and said rotatable hinge is adapted to be positioned adjacent to the rotatable joint and is adapted to rotate in correspondence with rotation of the rotatable joint when said strapping system is in said operative configuration, and wherein said first rigid support member is rotationally displaceable about said rotatable hinge relative to said second rigid support member.

4. The strapping system of claim 1, wherein the entirety of said first strap segment follows a three-dimensional spiral path when said strapping system is in said operative configuration.

5. The strapping system of claim 4, wherein the entirety of said second strap segment follows a two-dimensional semi-circular path when said strapping system is in said operative configuration.

6. The strapping system of claim 1, wherein said rigid support member includes a rigid first cuff, a rigid second cuff and a rigid elongate connective member, wherein said rigid first and second cuffs are positioned a separation distance apart from one another and are connected to one another by said rigid elongate connective member aligned coextensively with said separation distance, and wherein said first strap connector is positioned on said rigid first cuff and said second and third strap connectors are positioned on said rigid second cuff.

7. The strapping system of claim 6, wherein said second strap connector, said third strap connector and said rigid first cuff are fixedly positioned relative to one another in all configurations of said strapping system.

8. The strapping system of claim 6, wherein said rigid first cuff has a first arcuate shape adapted to conform to a first arcuate contour of the body and said rigid second cuff has a second arcuate shape adapted to conform to a second arcuate contour of the body.

9. The strapping system of claim 1, wherein said rigid support member has a first longitudinal edge and a second longitudinal edge opposite said first longitudinal edge, said first and third strap connectors are positioned on said first longitudinal edge and said second strap connector is positioned on said second longitudinal edge.

10. The strapping system of claim 9, wherein said fitted first strap end is positioned at said first longitudinal edge and said first strap segment is adapted to extend from said first longitudinal edge to said intermediate strap connection point positioned at said second longitudinal edge by initially extending away from said first longitudinal edge and said rigid support member and circling back to said second first longitudinal edge without overlappingly engaging said rigid support member, and wherein said first strap segment is adapted to maintain tensioned engagement with the body, thereby applying compression to the body where said first strap segment engages the body, when said strapping system is in said operative configuration.

11. The strapping system of claim 9, wherein said fitted second strap end is positioned at said first longitudinal edge and said second strap segment is adapted to extend from said first longitudinal edge to said intermediate strap connection point positioned at said second longitudinal edge by initially extending away from said first longitudinal edge and said rigid support member and circling back to said second first longitudinal edge without overlappingly engaging said rigid support member, and wherein said second strap segment is adapted to maintain tensioned engagement with the body, thereby applying compression to the body where said second strap segment engages the body, when said strapping system is in said operative configuration.

12. The strapping system of claim 1, wherein said strap is a unitary strap.

13. The strapping system of claim 1, wherein said second strap connector has a catch and said strap connection member has an opening sized and configured to releasably receive said catch, thereby enabling releasable attachment of said strap connection member to said second strap connector when said strapping system is in said operative configuration and detachment of said strap connection member from said second strap connector when said strapping system is in said non-operative configuration.

14. The strapping system of claim 1, wherein said first and second strap segments do not overlappingly engage said rigid support member when said strapping system is in said operative configuration.

15. The strapping system of claim 1, wherein said strap length remains fixed during sequential transition from said operative configuration to said non-operative configuration and back to said operative configuration.

16. A strapping system for an orthopedic brace comprising:
- a strap having a fitted first strap end, a free second strap end, a first fitted second strap end, a second fitted second strap end, a first fitted free second strap end coupling point, a second fitted free second strap end coupling point, a first fitted intermediate strap connection point and a second fitted intermediate strap connection point, wherein said first fitted intermediate strap connection point and said first fitted free second strap end coupling point are positioned on said strap between said fitted first strap end and said first fitted second strap end and said second fitted intermediate strap connection point and said second fitted free second strap end coupling point are positioned on said strap between said fitted first strap end and said second fitted second strap end;
- a strap coupler positioned at said free second strap end;
- a strap connection member slidably engaging said strap;
- a rigid support member having a first strap connector, a second strap connector and a third strap connector, wherein said first and third strap connectors are linearly aligned with one another to define a first-third strap connector line segment extending from said first strap connector to said third strap connector;
- wherein said strapping system is adapted to selectively transition between a first fitted operative configuration adapted to be worn on a body of a wearer, a second fitted operative configuration adapted to be worn on the body of the wearer or on a different body of a different wearer, a non-operative configuration adapted to be off any body of any wearer and a fit adjustment configuration adapted to adjust a fit of said strapping to the body or to the different body;
- when said strapping system is in said first fitted operative configuration: said strap is adapted to wrap around the body and retain said rigid support member in engagement with the body, said first fitted second strap end is substantially attached to said third strap connector, said strap connection member slidably engages said first fitted intermediate strap connection point and is releasably attached to said second strap connector, thereby effecting releasable substantial attachment of said first fitted intermediate strap connection point to said second strap connector, said fitted first strap end is substantially attached to said first strap connector, said fitted first strap end and said first fitted intermediate strap connection point bound a first fitted first strap segment having a first fitted first strap segment length, said first fitted intermediate strap connection point and said first fitted second strap end bound a first fitted second strap segment contiguous with said first fitted first strap segment and having a first fitted second strap segment length, said free second strap end is threaded through said third strap connector, doubled back over said first fitted second strap segment to said first fitted free second strap end coupling point positioned on said first fitted second strap segment and releasably coupled with said first fitted free second strap end coupling point via said strap coupler, wherein said first fitted first strap segment, said first fitted second strap segment and said first-third strap connector line segment in combination define a first triangular shape and said first fitted first strap segment length and said first fitted second strap segment length have a sum defining a first fitted strap length;
- when said strapping system is in said second fitted operative configuration: said strap is adapted to wrap around the body and retain said rigid support member in engagement with the body, said second fitted second strap end is substantially attached to said third strap connector, said strap connection member slidably engages said second fitted intermediate strap connection point and is releasably attached to said second strap connector, thereby effecting releasable substantial attachment of said second fitted intermediate strap connection point to said second strap connector, said fitted first strap end is substantially attached to said first strap connector, said fitted first strap end and said second fitted intermediate strap connection point bound a second fitted first strap segment having a second fitted first strap segment length, said second fitted intermediate strap connection point and said second fitted second strap end bound a second fitted second strap segment contiguous with said second fitted first strap segment and having a second fitted second strap segment length, said free second strap end is threaded through said third strap connector, doubled back over said second fitted second strap segment to said second fitted free second strap end coupling point positioned on said second fitted second strap segment and releasably coupled with said second fitted free second strap end coupling point via said strap coupler, wherein said second fitted first strap segment, said second fitted second strap segment and said first-third strap connector line segment in combination define a second triangular shape and said second fitted first strap segment length and said second fitted second strap segment length have a sum defining a second fitted strap length;
- when said strapping system is in said non-operative configuration: said strap connection member is detached from said second strap connector, thereby effecting detachment of said strap from said second strap connector, adapting said strap to unwrap from around the body and adapting said rigid support member to disengage from the body, further when said strapping system is in said non-operative configuration: said first fitted second strap end is substantially attached to said third strap connector, said strap connection member slidably engages said strap, said fitted first strap end is substantially attached to said first strap connector and said free second strap end is threaded through said third strap connector, doubled back over said first fitted second strap segment to said first fitted free second strap end coupling point and releasably coupled with said first fitted free second strap end coupling point;
- when said strapping system is in said fit adjustment configuration: said free second strap end is uncoupled from said strap, said third strap connector and said strap connection member slidably engage said strap and said fitted first strap end is substantially attached to said first strap connector;

wherein said strapping system is adapted to transition from said first fitted operative configuration to said non-operative configuration by detaching said strap connection member from said second strap connector, thereby detaching said strap from said second strap connector, adapting said strap to unwrap from around the body and adapting said rigid support member to disengage from the body;

wherein said strapping system is adapted to transition from said non-operative configuration back to said first fitted operative configuration by adapting said rigid support member to re-engage with the body, adapting said strap to re-wrap around the body and releasably re-attaching said strap connection member to said second strap connector, thereby effecting releasable substantial re-attachment of said first fitted intermediate strap connection point to said second strap connector;

wherein said first fitted second strap end remains substantially attached to said third strap connector, said strap connection member slidably engages said strap, said fitted first strap end remains substantially attached to said first strap connector and said free second strap end remains threaded through said third strap connector, doubled back over said first fitted second strap segment to said first fitted free second strap end coupling point and releasably coupled with said first fitted free second strap end coupling point during sequential transition from said first fitted operative configuration to said non-operative configuration and back to said first fitted operative configuration;

wherein said strapping system is adapted to sequentially transition from said first fitted operative configuration to said fit adjustment configuration and to said second fitted operative configuration by uncoupling said free second strap end from said first fitted free second strap end coupling point, aligning said free second strap end with said second fitted free strap end coupling point while said free second strap end is threaded through said third strap connector, releasably coupling said free second strap end with said second fitted free second strap end coupling point and sliding said strap connection member along said strap from said first fitted intermediate strap connection point into engagement with said second fitted intermediate strap connection point, thereby fixing said second fitted strap length; and wherein said third strap connector and said strap connection member slidably engage said strap and said fitted first strap end remains substantially attached to said first strap connector during sequential transition from said first fitted operative configuration to said fit adjustment configuration and to said second fitted operative configuration.

17. The strapping system of claim 16, wherein said strap is a unitary strap.

18. The strapping system of claim 16, wherein said fit adjustment configuration is a first fit adjustment configuration;

said strap further has first fitted paired intermediate strap connection points, second fitted paired intermediate strap connection points, a third fitted second strap end and a fourth fitted second strap end;

said strapping system further comprises a strap adjustment ring slidably engaging said strap and a ring coupler positionable at said strap adjustment ring and is further adapted to selectively transition between a third fitted operative configuration, a fourth fitted operative configuration and a second fit adjustment configuration;

when said strapping system is in said third fitted operative configuration: said strap is adapted to wrap around the body and retain said rigid support member in engagement with the body, said third fitted second strap end is substantially attached to said third strap connector, said strap connection member slidably engages said first fitted paired intermediate strap connection points and is releasably attached to said second strap connector, thereby effecting releasable attachment of said first fitted paired intermediate strap connection points to said second strap connector, said fitted first strap end is substantially attached to said first strap connector, said fitted first strap end and said first fitted paired intermediate strap connection points bound a third fitted first strap segment having a third fitted first strap segment length, said first fitted paired intermediate strap connection points and said third fitted second strap end bound a third fitted second strap segment having a third fitted second strap segment length, said free second strap end is threaded through said third strap connector, doubled back over said third fitted second strap segment to a third fitted free second strap end coupling point positioned on said third fitted second strap segment and releasably coupled with said third fitted free second strap end coupling point via said strap coupler, said strap is double threaded through said strap connection member to form a first fitted strap overlap loop overlapping said third fitted first strap segment and bounded by said first fitted paired intermediate strap connection points and a first fitted ring point where said strap slidably engages said strap adjustment ring, said first fitted ring point and said strap adjustment ring are doubled back over said third fitted first strap segment to a first fitted ring point coupling point positioned on said third fitted first strap segment, said first fitted ring point is releasably coupled with said first fitted ring point coupling point via said ring coupler, said third fitted first strap segment, said third fitted second strap segment and said first-third strap connector line segment in combination define a third triangular shape and said third fitted first strap segment length and said third fitted second strap segment length have a sum defining a third fitted strap length;

when said strapping system is in said fourth fitted operative configuration: said strap is adapted to wrap around the body and retain said rigid support member in engagement with the body, said fourth fitted second strap end is substantially attached to said third strap connector, said strap connection member slidably engages said second fitted paired intermediate strap connection points and is releasably attached to said second strap connector, thereby effecting releasable attachment of said second fitted paired intermediate strap connection points to said second strap connector, said fitted first strap end is substantially attached to said first strap connector, said fitted first strap end and said second fitted paired intermediate strap connection points bound a fourth fitted first strap segment having a fourth fitted first strap segment length, said second fitted paired intermediate strap connection points and said fourth fitted second strap end bound a fourth fitted second strap segment having a fourth fitted second strap segment length, said free second strap end is threaded through said third strap connector, doubled back over said fourth fitted second strap segment to a fourth fitted free second strap end coupling point positioned on said fourth fitted second strap segment and releasably coupled with said fourth fitted free second strap end coupling point via said strap coupler, said strap is double threaded through said strap connection member to form a second fitted strap overlap loop overlapping said fourth fitted first strap segment and bounded by said second fitted paired intermediate strap connection points and a second fitted ring point where said strap slidably engages said strap adjustment ring, said second fitted ring point and said strap adjustment ring are doubled back over said fourth fitted first strap segment to a second fitted ring point coupling point positioned on said fourth fitted first strap segment, said second fitted ring point is releasably coupled with said second fitted ring point coupling point via said ring coupler, said fourth fitted first strap segment, said fourth fitted second strap segment and said first-third strap connector line segment in combination define a fourth triangular shape and said fourth fitted first strap segment length and said fourth fitted second strap segment length have a sum defining a fourth fitted strap length;

when said strapping system is in said second fit adjustment configuration: said first and second fitted ring points are uncoupled from said first and second fitted ring point coupling points, respectively, said free second strap end is coupled with said first or second fitted free second strap end coupling point, said fitted first strap end is substantially attached to said first strap connector, said strap connection member slidably engages said strap and said first or second fitted second strap end is substantially attached to said third strap connector;

wherein said strapping system is adapted to sequentially transition from said third fitted operative configuration to said second fit adjustment configuration and to said fourth fitted operative configuration by uncoupling said first fitted ring point from said first fitted ring point coupling point, aligning said second fitted ring point and said strap adjustment ring with said second fitted ring point coupling point positioned on said third fitted second strap segment while said strap is threaded through said strap adjustment ring, releasably coupling said second fitted ring point with said second fitted ring point coupling point, thereby fixing said fourth fitted strap length; and wherein said first strap connector, said strap connection member and said strap adjustment ring slidably engage said strap and said first or second fitted second strap end remains substantially attached to said third strap connector during sequential transition from said third fitted operative configuration to said second fit adjustment configuration and to said fourth fitted operative configuration.

19. The strapping system of claim 16, wherein said first fitted strap length remains fixed during sequential transition from said first fitted operative configuration to said non-operative configuration and back to said first fitted operative configuration.

20. A strapping system for an orthopedic brace comprising:

a strap having a fitted first strap end, a fitted second strap end and a fitted intermediate strap connection point between said fitted first and second strap ends;

a strap connection member slidably engaging said strap;

a first rigid support member having a rigid first cuff, a rigid second cuff, a rigid elongate connective member, a first strap connector, a second strap connector and a third strap connector, wherein said rigid first and second cuffs are positioned a separation distance apart from one another and are connected to one another by said rigid elongate connective member aligned coextensively with said separation distance, and wherein said first strap connector is positioned on said rigid first cuff and said second and third strap connectors are positioned on said rigid second cuff;

a second rigid support member;

a rotatable hinge rotatably connecting said first and second rigid support members;

wherein said strapping system is adapted to selectively transition between an operative configuration adapted to be worn on a body of a wearer and a non-operative configuration adapted to be off any body of any wearer;

when said strapping system is in said operative configuration: said strap is adapted to wrap around a limb of the body and retain said first rigid support member in engagement with the limb, said first rigid support member is adapted to be positioned on a first side of a rotatable joint of the body in engagement with the limb rotationally displaceable about the rotatable joint and adapted to move in correspondence with the limb, said second rigid support member is adapted to be positioned on a second side of the rotatable joint opposite the first side in engagement with the body and said rotatable hinge is adapted to be positioned adjacent to the rotatable joint and adapted to rotate in correspondence with rotation of the rotatable joint, said first rigid support member is rotationally displaceable about said rotatable hinge relative to said second rigid support member, said fitted first strap end is substantially attached to said first strap connector, said strap connection member slidably engages said fitted intermediate strap connection point and is releasably attached to said second strap connector, thereby effecting releasable substantial attachment of said fitted intermediate strap connection point to said second strap connector, said fitted second strap end is substantially attached to said third strap connector, said fitted first strap end and said fitted intermediate strap connection point bound a first strap segment having a first strap segment length, said fitted intermediate strap connection point and said fitted second strap end bound a second strap segment contiguous with said first strap segment and having a second strap segment length, said first strap segment, said second strap segment and said first-third strap connector line segment in combination define a triangular shape and said first strap segment length and said second strap segment length have a sum defining a strap length;

when said strapping system is in said non-operative configuration: said strap connection member is detached from said second strap connector, thereby effecting detachment of said strap from said second strap connector, said strap is adapted to unwrap from around the limb and said first rigid support member is adapted to disengage from the limb, said fitted first strap end is substantially attached to said first strap connector, said strap connection member slidably engages said strap and said fitted second strap end is substantially attached to said third strap connector;

wherein said strapping system is adapted to transition from said operative configuration to said non-operative configuration by detaching said strap connection member from said second strap connector, thereby detaching said strap from said second strap connector, adapting said strap to unwrap from around the limb and adapting said first rigid support member to disengage from the limb;

wherein said strapping system is adapted to transition from said non-operative configuration back to said operative configuration by adapting said first rigid support member to re-engage with the limb, adapting said strap to re-wrap around the limb and releasably re-attaching said strap connection member to said second strap connector, thereby effecting releasable substantial re-attachment of said fitted intermediate strap connection point to said second strap connector; and wherein said fitted first strap end remains substantially attached to said first strap connector, said strap connection member slidably engages said strap and said fitted second strap end remains substantially attached to said third strap connector during transition from said operative configuration to said non-operative configuration.

21. A thigh strapping system for retaining a rigid support member of an orthopedic hip brace in a desired utilitarian position on a thigh of a wearer comprising:

a thigh strap having a fitted first strap end, a fitted second strap end and a fitted intermediate strap connection point between said fitted first and second strap ends;

a strap connection member slidably engaging said thigh strap;

a rigid support member having a first strap connector, a second strap connector and a third strap connector, wherein said first and third strap connectors are linearly aligned with one another to define a first-third strap connector line segment extending from said first strap connector to said third strap connector;

wherein said thigh strapping system is adapted to selectively transition between an operative configuration adapted to be worn on a thigh of a wearer and a non-operative configuration adapted to be off the thigh of the wearer;

when said thigh strapping system is in said operative configuration: said thigh strap is adapted to wrap around the thigh and retain said rigid support member in engagement with the thigh, said fitted first strap end is substantially attached to said first strap connector, said strap connection member slid ably engages said fitted intermediate strap connection point and is releasably attached to said second strap connector, thereby effecting releasable substantial attachment of said fitted intermediate strap connection point to said second strap connector, said fitted second strap end is substantially attached to said third strap connector, said fitted first strap end and said fitted intermediate strap connection point bound a first strap segment having a first strap segment length, said fitted intermediate strap connection point and said fitted second strap end bound a second strap segment contiguous with said first strap segment and having a second strap segment length, said first strap segment, said second strap segment and said first-third strap connector line segment in combination define a triangular shape and said first strap segment length and said second strap segment length have a sum defining a strap length;

when said thigh strapping system is in said non-operative configuration: said strap connection member is detached from said second strap connector, thereby effecting detachment of said thigh strap from said second strap connector, said thigh strap is adapted to unwrap from around the thigh and said rigid support member is adapted to disengage from the thigh, said fitted first strap end is substantially attached to said first strap connector, said strap connection member slidably engages said thigh strap and said fitted second strap end is substantially attached to said third strap connector;

wherein said thigh strapping system is adapted to transition from said operative configuration to said non-operative configuration by detaching said strap connection member from said second strap connector, thereby detaching said thigh strap from said second strap connector, adapting said thigh strap to unwrap from around the thigh and adapting said rigid support member to disengage from the thigh;

wherein said thigh strapping system is adapted to transition from said non-operative configuration back to said operative configuration by adapting said rigid support member to re-engage with the thigh, adapting said thigh strap to re-wrap around the thigh and releasably re-attaching said strap connection member to said second strap connector, thereby effecting releasable substantial re-attachment of said fitted intermediate strap connection point to said second strap connector; and wherein said fitted first strap end remains substantially attached to said first strap connector, said strap connection member slidably engages said thigh strap and said fitted second strap end remains substantially attached to said third strap connector during transition from said operative configuration to said non-operative configuration.

* * * * *